(12) United States Patent
Gault

(10) Patent No.: US 7,314,375 B2
(45) Date of Patent: Jan. 1, 2008

(54) PROVISIONAL DENTAL IMPLANT FOR PREPARING AN ALVEOLUS

(75) Inventor: Philippe Gault, Orleans (FR)

(73) Assignee: Henkel KGaA, Dusseldorf (DE)

( * ) Notice: Subject to any disclaimer, the term of this patent is extended or adjusted under 35 U.S.C. 154(b) by 386 days.

(21) Appl. No.: 10/466,079

(22) PCT Filed: Jan. 11, 2002

(86) PCT No.: PCT/FR02/00097

§ 371 (c)(1),
(2), (4) Date: Jul. 11, 2003

(87) PCT Pub. No.: WO02/054973

PCT Pub. Date: Jul. 18, 2002

(65) Prior Publication Data

US 2004/0067467 A1    Apr. 8, 2004

(30) Foreign Application Priority Data

Jan. 12, 2001    (FR)    ................... 01 00404

(51) Int. Cl.
*A61C 8/00* (2006.01)
(52) U.S. Cl. ................... 433/173; 433/201.1
(58) Field of Classification Search ........ 433/172–176, 433/201.1, 80; 623/23.49
See application file for complete search history.

(56) References Cited

U.S. PATENT DOCUMENTS

| | | | |
|---|---|---|---|
| 4,051,598 A | | 10/1977 | Sneer |
| 4,186,486 A | | 2/1980 | Gordon |
| 4,252,525 A | * | 2/1981 | Child ........................ 433/173 |
| 4,671,768 A | * | 6/1987 | Ton ............................ 433/174 |
| 5,090,903 A | * | 2/1992 | Taylor et al. ................ 433/80 |
| 5,197,882 A | * | 3/1993 | Jernberg .................... 433/215 |
| 5,383,935 A | * | 1/1995 | Shirkhanzadeh ......... 623/23.49 |
| 5,499,918 A | * | 3/1996 | Morgan et al. ............. 433/173 |
| 5,584,688 A | * | 12/1996 | Sakuma et al. .............. 433/81 |
| 5,890,902 A | * | 4/1999 | Sapian ........................ 433/173 |
| 6,132,214 A | | 10/2000 | Suhonen et al. |
| 6,159,010 A | | 12/2000 | Rogers et al. |
| 6,299,448 B1 | * | 10/2001 | Zdrahala et al. ........... 433/173 |
| 6,309,220 B1 | * | 10/2001 | Gittleman .................. 433/173 |

FOREIGN PATENT DOCUMENTS

| | | |
|---|---|---|
| DE | 35 33 395 | 5/1986 |
| DE | 197 41 087 | 4/1999 |
| WO | WO 99/39651 | 8/1999 |
| WO | WO 00/21456 | 4/2000 |

\* cited by examiner

*Primary Examiner*—John J Wilson
(74) *Attorney, Agent, or Firm*—Nixon & Vanderhye P.C.

(57) ABSTRACT

The present invention relates to a temporary dental implant intended to prepare the alveola of an extracted tooth so that a selected dental implant can be inserted later. It also involves the use of this temporary dental implant from a functional and/or aesthetic point of view. It has, in addition, as its object kits, methods and tools, notably resin models, that can be used for the application or preparation of the above implants.

20 Claims, 4 Drawing Sheets

PROVISIONAL DENTAL IMPLANT FOR PREPARING AN ALVEOLUS

This application is the US national phase of international application PCT/FR02/00097 filed 11 Jan. 2002 which designated the U.S.

BRIEF SUMMARY OF THE INVENTION

The present invention relates to a temporary dental implant intended to prepare the alveola of an extracted tooth with the intention of installing subsequently a selected dental implant. It also relates to the use of this temporary dental implant from a medical, functional and/or aesthetic viewpoint. It also relates to kits, methods and tools, especially resin models, used for the application, preparation or morphological selection of the above implants.

The natural tooth is anchored in a cavity called the alveola, in the maxillary bone. This tooth is extracted when it is affected by lesions that are too serious to be treated: deep caries, parodontal pouch, rift, fractures, abscesses, traumatic injury. The insertion of a dental implant can in such cases be the best solution applicable for its replacement.

The implantation is the result of a prudent and considered step the aim of which is to create ties to the maxilla or the mandible which will be stable, resistant, effective, non iatrogenic and durable and on which is fitted a detachable or fixed prosthesis offering the patient who is partially or completely toothless, adequate function, satisfactory comfort and an aesthetic appearance suitable for social function.

As far as the implantation is concerned, two techniques are basically used at the present time:

a) The prostheses on osteo-integrated implants which are artificial roots made of titanium and which are stabilized by bone ankylosis. The masticatory force is transmitted to the bone without any reduction in power, due to the absence of the alveolo-dental ligament which is an important factor in protecting the teeth against impact, overload, and the risk of fracture.

b) The transplants or other dental grafts, which do not have the disadvantages of the above approach but require the availability of a suitable adequate and generally non functional donor tooth.

Dental transplantations and reimplantations have been carried out for several decades and a variety of techniques have been described.

Another possible technique, described recently in the patent application WO 00/21456, proposes the replacement of lost teeth by permanent false teeth connected to the maxillaries by the same tissue elements as natural teeth, i.e. a cement, an alveolo-dental ligament and an alveolar bone and allowing normal attachment of the gum to the neck of the implant. This technique allows the periodontium to exert advantageously its normal physiological role, which is basically to dampen the impact of mastication.

For a long time, oral implants have been synonymous with complications.

The technique of oral implantation actually comprises the risks of failures and contra-indications mainly associated with deficiencies in the bone involving its volume and density, poor vascular supply to certain bone regions, possible overheating of tissues during the drilling of the alveolas which can result in peri-implant tissue necrosis, and infections basically associated with buccal flora or radicular debris or dental filler sometimes left in the bone after extraction.

Previous careful examination, previous buccal cleaning, dental and parodontal, antibiotic cover during the procedure, a surgical protocol that complies with the rules and findings based on scientific experience allows the risk of failure to be kept below 5%.

Thus, the present invention proposes, for the first time, a solution allowing the risk of failure to be reduced while allowing biological stimulation of the tissues. It involves a temporary alveolar dental preparation implant intended to receive the final implant. It operates both for osteo-integrable implants as well as implants with cement and alveolo-implant ligament (Patent WO 00/21456). The preparation implant consists of a coronary part and a radicular part, the latter being hollow and partially porous. The compartment created in the interior of the preparation implant is intended to contain an active composition that is released directly at the alveolar site presenting a risk of infection, via the pores or channels responsible for the porosity of the radicular part of the preparation implant.

Another advantage of the present invention is the conservation or remodeling of the size of the alveola adapted for the insertion of the implant selected at the start.

The alveolar preparation implant also allows control of the healing of the alveola in such a way as to optimize osteo-integration or parodonto-integration.

So, one initial aim of the present application involves a temporary alveolar dental preparation implant, characterized in that it forms a separable coronary part and a radicular part and in that the radicular part is hollow and partially porous. The dental implant according to the invention is a temporary implant, i.e. intended to prepare an alveola with the intention of inserting a definitive implant on a subsequent occasion. So, it is intended to be placed in a subject in a temporary manner, during the period of time needed for the preparation of the definitive implant, and allows preparation of the site of implantation to increase the success of the treatment, and to shorten the overall time of the process. Typically, it involves a temporary non-osteo-integrable implant, i.e. non integrated in a permanent manner in the bone.

Another aim of the present application involves the use of a dental implant comprising of a separable coronary part and a radicular part, the radicular part being hollow and partially porous, for the preparation of a composition or a kit intended for temporary implantation in a subject for the preparation of an alveola intended to receive a definitive implant. The temporary implantation means that the temporary implant is maintained in the alveola for a fixed period of time, typically from one to five months, for example from one to two months, then it is removed. Typically, it is non-osteo-integrable, i.e. non integrated in a permanent manner in the bone.

Another aim of the present application involves a method of dental implantation in a subject, comprising a preparation step for an alveola intended to receive a definitive implant by inserting a temporary implant comprising a separable coronary part and a radicular part, the radicular part being hollow and partially porous.

One particular method comprising (i) the extraction of an affected tooth, (ii) the insertion in the alveola of said tooth of a temporary implant comprising a separable coronary part and a radicular part, the radicular part being hollow and partially porous and (iii), the removal of the temporary implant and the insertion of a definitive implant in the alveola prepared in such a manner. Step (i) is optional in so far as the implantation can be carried out at a site from which the tooth has already been removed.

Another aim of the invention is also the preparation of a product or kit intended to promote maxillary or mandibular bone reconstruction in patients for whom the insertion of an implant would require a bone graft beforehand, an additional and complex surgical step, requiring an additional period of at least four months. So, the alveolar preparation implant allows control of the healing in an optimal manner, and, in the case of parodonto-integrable implants which require preparation in the laboratory using tissue engineering techniques, to maintain the appropriate morphology of the alveola during the period needed for the in vitro steps.

Other aspects of the present application involve particularly disposable models of teeth which can be used as a gauge, as well as in kits, comprising for example several sets of temporary implants or disposable models.

DETAILED DESCRIPTION OF THE INVENTION

Structure and Materials Involved in the Alveolar Dental Preparation Implant:

The present invention involves an alveolar dental preparation implant intended to receive the definitive implant. The preparation implant consists of a separable coronary part ((1) of FIG. 4) and a radicular part ((2) of FIG. 4).

Figure 4:
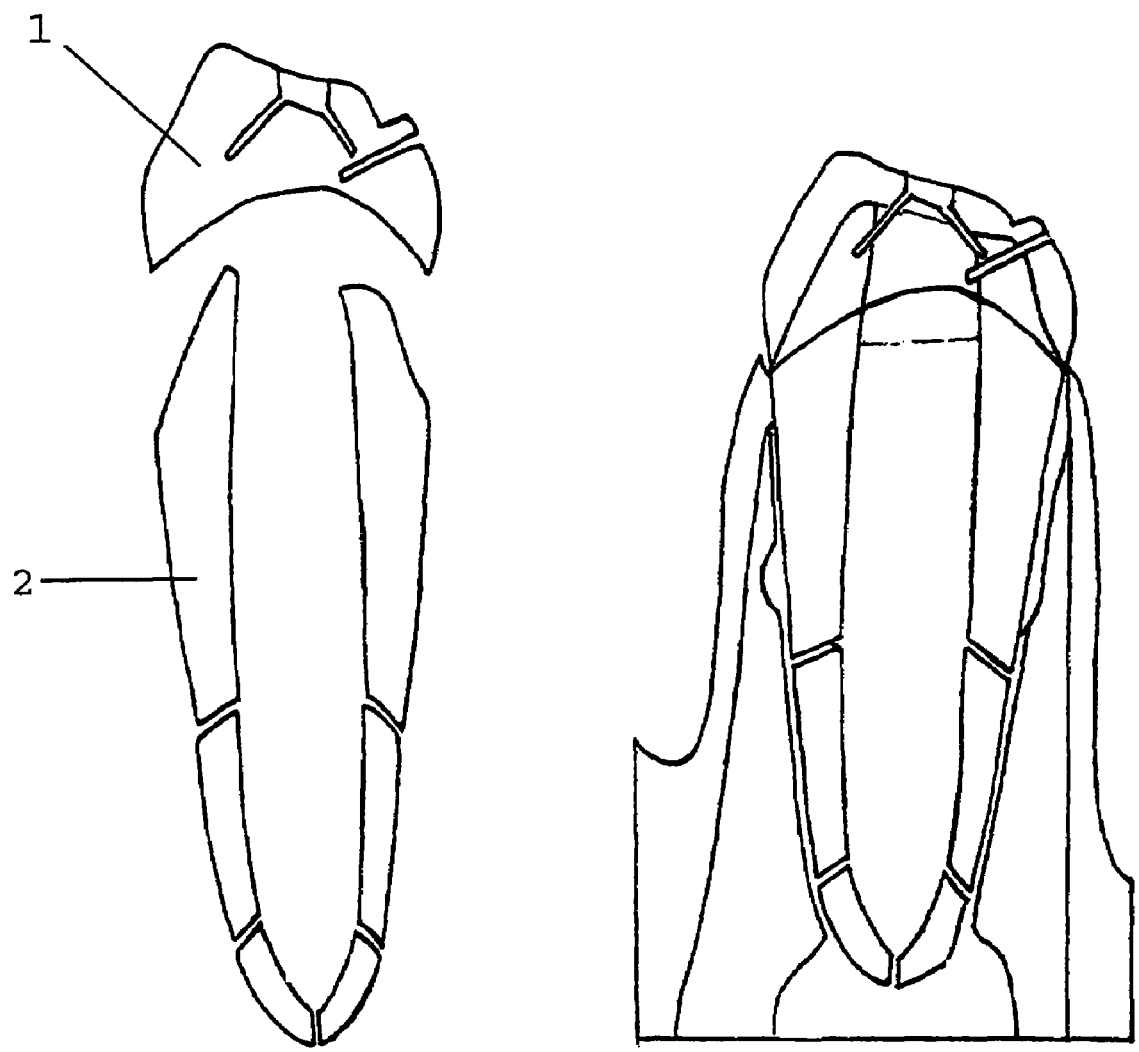
FIG. 4: Temporary alveolar dental preparation implant. It allows the size of the alveola to be maintained suitable for the insertion of the definitive implant determined at the start, and controls the healing process. It is hollow, to allow, via pores, slow release of active material which will prepare the site for receiving the definitive implant. It is covered and sealed by a crown of resin or grooved composite, for example, which can be sutured to the gum ((g) in FIG. 1) or stuck to the neighboring teeth. This configuration allows the immediate replacement of the extracted tooth for cosmetic reasons. Coronary and radicular parts are shown ((1) and (2), respectively).

The coronary part ((1) of FIG. 4) covers and seals the radicular part ((2) of FIG. 4). The seal can be ensured by any type of material allowing a temporary attachment of the two parts of the implant. According to one preferred embodiment of the invention, the two parts are linked by a temporary cement. According to another preferred embodiment of the invention, the coronary part ((1) of FIG. 4) is fitted, on its palatine face, with a channel which the operator can use to support an instrument, since, by carrying out a lever movement, he can separate more easily, the coronary part ((1) of FIG. 4) from the radicular part ((2) of FIG. 4), if required.

The coronary part ((1) of FIG. 4) of the preparation implant is adapted to the radicular part ((2) of FIG. 4) of this implant, selected on the basis of the extracted tooth to be replaced, and can be made of any biocompatible material mechanically suitable. It can involve for example a simple methyl-methacrylate resin. According to one preferred embodiment of the invention, the coronary part ((1) of FIG. 4) is made of a composite material. According to another preferred embodiment of the invention, the crown is made of a composite material based on loaded methylmethacrylate resin.

Figure 1:
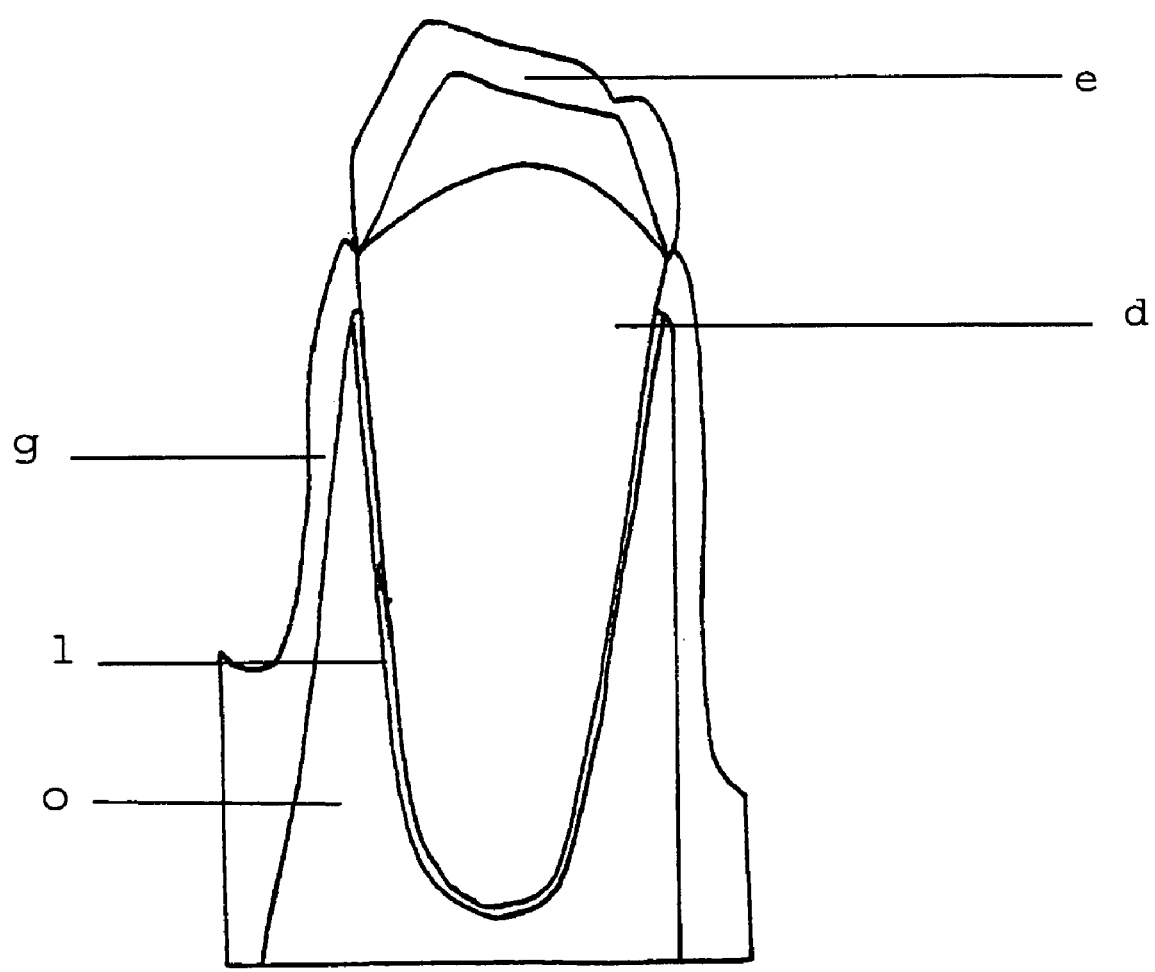
FIG. 1: Scheme of a section of a natural tooth: enamel (e), dentine (d), maxillary bone (o), gum (g), ligament (I). The ligament defines the dental alveola.
Figure 2:
FIG. 2: Scheme of a section of a tooth affected by lesions that are too serious for treatment: deep caries, parodontal pouch, splitting, fracture, abscess, traumatic injury.

This crown can be attached to the neighboring teeth to stabilize the temporary implant. As an alternative, this crown can be held by sutures to the gum ((g) in FIG. 1) and so keep the radicular part ((2) of FIG. 4) in the alveola. In this case, the crown comprises channels and/or grooves that act to stabilize the sutures (cf: Drawing no. 1). This crown is adjusted to remain in sub-occlusion during all movements of the mandible, such that the sub-adjacent tissues can undergo healing without being subject to significant compression. It also has the aesthetic advantage of allowing immediate replacement of an extracted tooth following the selection of the suitable morphological model. The sutures used can be any type of bio-degradable or non biodegradable material with a functional life of at least four to five weeks. According to one preferred embodiment of the invention, the sutures used are made of non biodegradable teflon.

The radicular part ((2) of FIG. 4) of the temporary implant can have a variety of shapes and dimensions, basically determined by the type of tooth and by the type of implant.

In the case where a defined parodonto-integrable implant is planned, the radicular part ((2) of FIG. 4) of the preparation implant has an overall shape matching that of the extracted tooth that is to be replaced. However, it is also possible to alter the alveola, for example with bone drills, after the tooth extraction, to fit as closely as possible one of the shape models available. The model and the preparation implant will be slightly greater than the definitive implant with cement and ligament ((I) in FIG. 1), to leave a space of 50 to 300 micrometers, for example, intended for the development of the ligament ((I) in FIG. 1) and the alveolar bone attaching the ligament ((I) in FIG. 1) to the rest of the maxilla. This space avoids the formation of permanent compression zones between the implant root and the maxillary bone ((o) in FIG. 1) during the insertion of the definitive parodonto-integrable implant.

In the case where the planned definitive implant is osteo-integrable, the shape of the alveolar preparation implant is generally cylindrical or slightly conical or with steps according to the type of implant envisaged. Its length is that of the definitive implant envisaged. On the other hand, its diameter is generally smaller, for example about 1 millimeter, to allow insertion in the healed bone of whorls of the definitive osteo-integrable implant and its good initial stability which is essential for a satisfactory outcome.

The radicular part ((2) of FIG. 4) of the alveolar preparation implant, according to the invention, can be of any biocompatible material which is sufficiently mechanically resistant to avoid the risk of fracture. According to a preferred method of the invention, the preparation root is made of biocompatible plastic, for example polycarbonate, polytetrafluoroethylene or methyl polymethacrylate.

The radicular part ((2) of FIG. 4) of the alveolar preparation implant, according to the invention, includes a cavity able to contain active composition. Furthermore, the radicular part ((2) of FIG. 4) includes holes or channels with a diameter sufficient to ensure effective diffusion of the active composition, in the alveola, for example over a period of 4 to 5 weeks, preferably 6 to 8 weeks.

The cavity in the radicular part ((2) of FIG. 4) of the alveolar preparation implant can, according to another embodiment of the invention, be divided into compartments and hence contain, in each compartment, a particular active composition which will act preferentially at a given alveolar region.

The number, position and diameter of the pores can be adjusted by a man skilled in the art, as a function of the type of tooth, the active composition, etc. In addition, it is also possible, according to the length of treatment, to refill the cavity of the radicular part ((2) of FIG. 4), by withdrawing it from the coronary part ((1) of FIG. 4), after implantation.

Active Material Released by the Radicular Part ((2) of FIG. 4) Part of the Alveolar Preparation Implant:

The active composition that the cavity, described in the last paragraph, can contain, can be, for example, in the form of a solid or liquid, in the form of a gel or paste or even in a micro-encapsulated form. It can contain any biologically active compound the release of which into the alveola is desired.

The active composition can contain:

One or more antibiotics, to decontaminate the implant site; it can be for example tetracycline. It can also be metronidazole.

an unsaponifiable material, for example maize, soya or avocado, which promotes collagenic healing, and/or a vitamin (with the same aim), and/or one or more growth factors, to accelerate healing, (for example PDGF, TGFb, IGF, EGF, BMP, amelogenins, etc.) and/or one or more hemostatic agents, and/or one or more hormones, like for example dexamethasone, promoting tissue mineralization, and/or one or more other compounds to prepare the site of the implant, if necessary obtained by genetic engineering.

Kits

The present invention also offers, in an advantageous manner, an assembly or kit comprising several radicular parts ((2) of FIG. 4) as defined above, of different sizes and/or shapes. More preferably, it involves a kit comprising radicular parts ((2) of FIG. 4) suited to the main tooth shapes encountered in human beings, more particularly to the 26 tooth shapes. According to the extracted tooth, the professional therefore has at his disposal a range of preparation implants, allowing him to select the most suitable.

Figure 3:
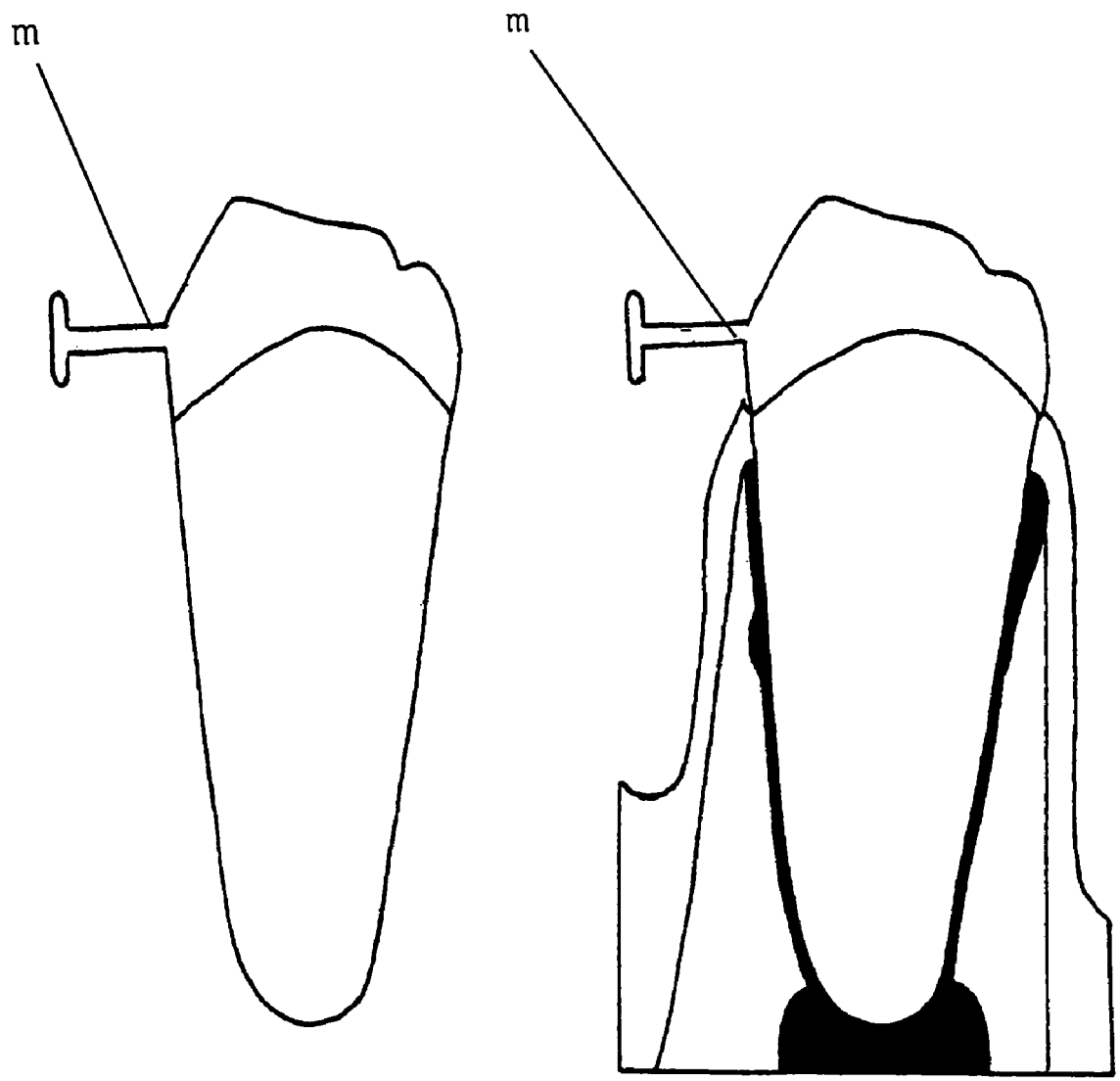
FIG. 3: Example of a disposable, resin model, including a means of gripping (m) located on the corresponding part to the coronary region of a tooth and allowing one to gauge after extraction of the affected tooth, the size of the preparation implant and hence the definitive implant required for the replacement of the tooth. This model can be monochrome but should allow the neck of the tooth to be seen to insert it in the gum ((g) in FIG. 1).

As indicated, the invention also provides tooth models (see FIG. 3), which can be used for example as a gauge. Typically, these models are disposable, and made of a biocompatible material, preferably in resin or a resin base. The model can have, on its vestibular face, a gripping spike ((m) in FIG. 3) which allows it to be manipulated by the professional using pincers or needle-holder tweezers, and a hole through which a safety wire can be threaded. The model can be monochrome, but it allows advantageously a view of the neck of the tooth to insert it in the gum ((g) in FIG. 1). Several models (up to 26), suited to the different types of morphology of the roots of a human being, allow the vast majority of requirements to be met. The professional will be able, with the help of the models available, to select the shape best suited to the alveolar preparation implant.

Thus, the present invention offers the professional a preparation kit for the insertion of a dental implant, which comprises:

1 or more models (preferably 26 models) allowing one to gauge the size and/or shape of the appropriate preparation implant and so that of the definitive implant, and/or 1 or more models (preferably 26 models) of alveolar preparation implants, of corresponding morphology or of radicular parts ((2) of FIG. 4) of such preparation implants, and/or 1 or more models (preferably 42 models) of grooved crowns, for the sutures and for sub-occlusion, and/or 1 or more models (preferably 42 models) of temporary crowns to control in sub-occlusion or occlusion (these crown can also serve as the definitive implant), and/or one or more active compositions, intended for insertion into the hollow radicular part ((2) of FIG. 4) of the alveolar preparation implant.

It is understood that these different items can be packaged in a variety of ways, for example in sachets, boxes, etc., preferably as single items, generally under sterile conditions.

Use/Insertion

The insertion of the alveolar preparation implant, according to the invention, comprises insertion of the radicular part ((2) of FIG. 4) and the coronary part ((1) of FIG. 4) which covers and seals the former.

The installation of the assembly can be helped by the previous use of one or more tooth models made in biocompatible material, as described above. The model allows one to gauge, after extraction of the tooth to be replaced, the size of the alveola, to modify it if required, and to select the preparation implant of the corresponding shape, as well as the future definitive implant.

After insertion, the temporary dental implant is held in place by any suitable technique (adhesive, suture, etc.). Preferably, it is held by suturing using thread in biodegradable material or by adhesion of the coronary part ((1) of FIG. 4) to the neighboring teeth, using a composite material.

When the definitive implant is ready and/or when the alveola intended to receive it has healed sufficiently, the temporary implant is removed and replaced by the definitive implant. This period is determined by the professional in terms of the individual case involved, and can range from several weeks to several months, generally 1 to 6 months, advantageously 1 to 3 months.

The subsequent repair of a tissue lesion (extraction, fracture, drilling of the alveola for example) goes through three successive phases, more or less overlapping: an inflammatory phase, a cell proliferation phase and a tissue remodeling phase.

The inflammatory phase triggers the process by contributing immunity-related components, the phagocytosis of the injured and destroyed materials and bacteria present, by activation of macrophages. This is an overall destructive phase.

The expansion of cytokines and growth factors, especially PDGF released by blood platelets during coagulation, initiates the following phases directed at tissue repair.

The growth factors that have a significant action on cell proliferation are PDGF, TGFb and IGF. After a tooth extraction, the cells that proliferate are the residual fibroblasts, peri-vascular undifferentiated cells and medullary bone cells. The proliferation phase starts after 48 hours and continues for 2 to 3 weeks after any trauma. It results in what is called granulation tissue which reaches a maximum around 8 days.

PDGF and IGF also have an effect on the chemotaxis—the migration—of these cells towards the lesion to recolonize it.

The differentiation of cells before they are able to reconstitute the tissue matrix is under the influence of many physico-chemical factors. Growth factors like EGF, IGF, TGF and BMP can have an effect, just like other more specific compounds like the amelogenins for example. Mechanical constraints also play an important role at this level.

The remodelling phase is the period where the cells that have ceased to proliferate produce the specific matrix or matrices for the tissues to be repaired. For example, in the periodontium, a population of fibroblasts will produce collagen which will re-establish the conjunctive fibers forming the tissue and giving it its resistance to tension and the osteoblasts will secrete the mineralizable matrix which will undertake the production of crystals of hydroxy-apatite to provide bone tissue. Cementoblasts coming into contact with the tooth roots, in the parodontal lesions, re-establish the connection between the conjunctive fibers and the radicular surface by the regeneration of a (<cement>).

As far as the established methods ofr osteo-integrated implantation techniques are concerned, the permitted interval in healing between the extraction of the tooth affected and the insertion of the implant intended to replace it is 6 to 12 months, increased by the period of osteo-integration which, itself, is 3 to 6 months (Adell et coll., 1981).

The alveolar preparation implant and the methods according to the invention, allow, by the release of suitable growth factors and a certain degree of physiological stimulation (reduced in comparison with the normal constraints usually undergone by a tooth), accelerated healing and better preparation of the site of insertion of the definitive implant, be it osteo or parodonto-integrated. If it is found that too much or not enough activation reduces the bone repair, the mechanical stimulation produced by the techniques of the invention involving the alveola are appropriate by the fact that the crown placed on the preparation implant is in sub-occlusion and only transmits part of the pressure induced by mastication.

Thus, the technique according to the invention allows a reduction in the normal healing time by a factor of about three, and improves the conditions of integration or insertion of the definitive implant.

I claim:

1. A method for preparing a dental alveola before subsequent insertion of a definitive implant in a subject, which method comprises, after tooth extraction, inserting a temporary implant comprising separable coronary and radicular parts, said radicular part being hollow, partially porous and consisting of polytetrafluoroethylene, whereby said temporary implant controls healing of the alveola without integration in the bone.

2. The method according to claim 1, wherein the coronary part covers and seals the radicular part with the help of a temporary cement.

3. The method according to claim 1, wherein the coronary part is made of biocompatible material.

4. The method according to claim 1, wherein the radicular part has a shape suited to that of the extracted tooth.

5. The method according to claim 1, wherein the radicular part has a shape suited to that of the extracted tooth and 50 to 300 micrometers larger than a parodonto-integrable definitive implant.

6. The method according to claim 1, wherein the radicular part has a cylindrical or slightly conical shape or with steps, suitable for receiving a particular osteo-integrable implant and slightly smaller than said implant.

7. The method according to claim 1, wherein the radicular part has a cylindrical or slightly conical shape or with steps, suitable for receiving a particular osteo-integrable implant.

8. The method according to claim 1, wherein the radicular part includes a cavity that contains one or more active compositions, said active composition containing a compound selected from the group consisting of an antibiotic, unsaponifiable maize, soya, avocado, a vitamin, a growth factor, an hemostatic agent, and an hormone.

9. A method of dental implantation in a subject, which method comprises (i) preparing a dental alveola by, after tooth extraction, inserting in said alveola a temporary implant comprising separable coronary and radicular parts, said radicular part being hollow and partially porous and capable of allowing the diffusion of one or more active substances (ii) removing said temporary implant and (iii) inserting a definitive implant in the alveola that has been so prepared.

10. The method according to claim 9, wherein the radicular part is made of polytetrafluoroethylene.

11. The method according to claim 9, wherein the coronary part covers and seals the radicular part with the help of a temporary cement.

12. The method according to claim 9, wherein the coronary part is made of biocompatible material.

13. The method according to claim 9, wherein the radicular part has a shape suited to that of the extracted tooth.

14. The method according to claim 9, wherein the radicular part has a shape suited to that of the extracted tooth and 50 to 300 micrometers larger than a parodonto-integrable definitive implant.

15. The method according to claim 9, wherein the radicular part has a cylindrical or slightly conical shape or with steps, suitable for receiving a particular osteo-integrable implant and slightly smaller than said implant.

16. The method according to claim 9, wherein the radicular part has a cylindrical or slightly conical shape or with steps, suitable for receiving a particular osteo-integrable implant.

17. The method according to claim 9, wherein the radicular part includes a cavity that contains one or more active compositions, said active composition containing a compound selected from the group consisting of an antibiotic, unsaponifiable maize, soya, avocado, a vitamin, a growth factor, an hemostatic agent, and an hormone.

18. The method according to claim 17, wherein the antibiotic is selected from tetracycline and metronidazole.

19. The method according to claim 17, wherein the hormone is dexamethasone.

20. The method according to claim 17, wherein the active composition further contains a compound, obtained by genetic engineering, preparing the receptor site of the implant.

* * * * *